United States Patent [19]

Meyrat et al.

[11] Patent Number: 4,900,512

[45] Date of Patent: Feb. 13, 1990

[54] APPARATUS FOR PHOTOMETRICALLY ANALYSING LIQUID SAMPLES

[75] Inventors: Pierre-André Meyrat; Alain Oppliger, both of La Chaux-de-Fonds; Denis Steiner, St-Imier, all of Switzerland

[73] Assignee: Nivarox-Far S.A., Le Locle, Switzerland

[21] Appl. No.: 136,668

[22] Filed: Dec. 22, 1987

[30] Foreign Application Priority Data

Dec. 24, 1986 [FR] France ............................... 86 18255

[51] Int. Cl.[4] ............................................. G01N 21/00
[52] U.S. Cl. ......................................... 422/63; 436/52; 436/180
[58] Field of Search ................... 422/62–67, 422/82, 52, 58, 100; 436/43, 52, 53, 180; 73/864.81; 222/386.5, 632, 95, 442

[56] References Cited

U.S. PATENT DOCUMENTS

| 4,383,041 | 5/1983 | Kutsusawa et al. | 422/63 |
| 4,436,822 | 3/1984 | Eseifan | 422/63 |
| 4,503,012 | 3/1985 | Starr | 422/63 |
| 4,520,108 | 5/1985 | Yoshida et al. | 422/63 |

Primary Examiner—Barry S. Richman
Assistant Examiner—T. J. Wallen
Attorney, Agent, or Firm—Sughrue, Mion, Zinn, Macpeak & Seas

[57] ABSTRACT

An apparatus for photometrically analyzing liquid samples comprises a capsule (1) in which a measuring cell (7) is housed. This cell is inserted in a flow circuit for liquid samples delivered from containers (R) travelling on a conveyor (17). Each sample is taken up by a pivoting arm (15) and with the aid of a pump (13). The volume of the measuring cell (7) is so calculated that the quantity of liquid sample contained in the containers (R) is sufficient firstly to rinse the cell with this liquid then for the measurement to be carried out. A particular application is the measurement of bioluminescence reactions produced in samples containing living organisms.

13 Claims, 2 Drawing Sheets

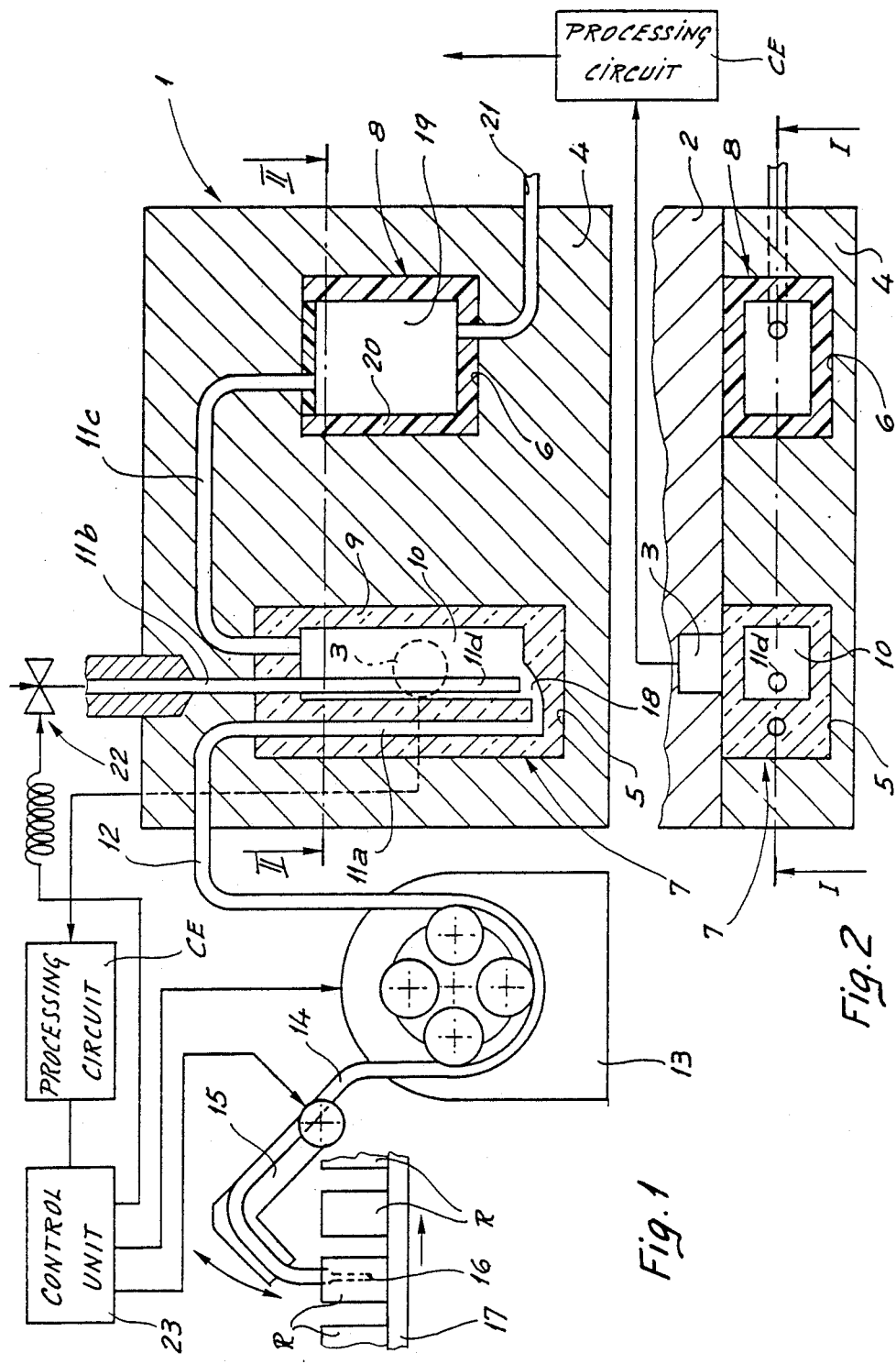

APPARATUS FOR PHOTOMETRICALLY ANALYSING LIQUID SAMPLES

BACKGROUND OF INVENTION

This invention relates to an apparatus for photometrically analysing liquid samples.

The successive analysis of a large number of samples is faced with the difficulty of preventing the measurement in progress from being spoiled by residues remaining in the apparatus after measurement of the preceding sample. For example, the concentration or the composition of a sample may be modified by these residues and produce an error in the resulting measurement. This is in particular the case for apparatus measuring the properties of samples by photometry.

In a known apparatus of this type sold under the reference XP-2000 by Skan AG of 4009 Basel-Allschwil, Switzerland, the photometric measurement is carried out while the sample is located in a chamber isolated from ambient light. This chamber is defined in a plate screwed to the front of a housing containing a photomultiplier and appropriate electronic circuits which transform the signal supplied by the photomultiplier into data which the user can exploit. The apparatus in question is intended typically for the measurement of bioluminescence produced by the reaction of an enzyme on a liquid sample mixed with a certain quantity of living organisms such as bacteria. However, very similar difficulties may be encountered in the analysis of a liquid by for example measuring its transparency to light. The photomultiplier thus for example serves to measure the light which reaches it through the liquid from a light source opposite the photomultiplier.

A detailed description of the method of analysis by bioluminescence is found in an article by N. Maire in the publication "Soil Biol. Biochem." vol. 16, no. 4, pp. 361-366, 1984. In summary, it involves analysing a medium, such as soil, by first extracting the ATP molecule from the medium's cells by rupturing the cells' walls and then photometrically measuring the molecule by an enzymatic bioluminescence reaction. This is made possible because the intensity of the light emitted during this reaction is directly proportional tot he concentration of ATP and because this concentration is representative of the biological activity of the soil sample under examination, ATP being a mononucleotide of the metabolism that is found in all living organisms and which ensures the transmission or the storage of energy in most biochemical reactions taking place in living cells (respiration, fermentation, photosynthesis, etc.)

To obtain a faithful evaluation of bioluminescence, it is nonetheless necessary to carefully avoid contamination of a sample during analysis by a sample which has just been analysed.

In the known apparatus mentioned above, this requirement is satisfied by rinsing the measurement cell with a rinsing liquid. But to accomplish this, the assembly plate must be taken off the capsule, the cell removed from the latter and rinsed, followed by a reassembly operation. This method therefore does not lend itself to rapid and automatic processing of a large number of samples.

SUMMARY OF INVENTION

An object of the invention is to provide a photometric analysis apparatus of the above-described type but which is adapted to the automatic successive processing of a large number of samples without it being possible for the samples, between themselves, to perturb the analysis results obtained.

The analysis apparatus provided by the invention comprises a measurement cell disposed in a light-proof enclosure, adapted to successively receive liquid samples, a photometric detector near the measurement cell to receive a light signal representing a property of the sample and measurement processing means connected to said detector to convert the signal supplied by the detector into data providing a visual representation of said property, wherein said cell is placed in a flow circuit for successive liquid samples which comprises means for successively taking in said samples, and a pump between said latter means and said cell, the volume of said measurement cell being at most equal to the volume of each sample having to be analysed.

As a result of these features, the measurement cell can be rinsed by flowing the sample therein until there is an overflow, after which it is certain that no further trace of the previously analysed sample remains in the cell. Hence, it suffices to fill the measurement cell and to start measuring once it is full. Of course, it is preferred to work with successive samples having a volume substantially greater than that required to just fill the measurement cell. The rinsing can thus be made to last longer thereby improving the rinsing action.

It can thus be seen that the analysis procedure can be automated since the measurement cell can remain connected in the sample flow circuit. Furthermore, neither a special rinsing liquid, nor special valves or ducts to supply such liquid to the cell or remove it, are necessary.

BRIEF DESCRIPTION OF DRAWINGS

The invention will be better understood from the following description of an embodiment thereof. In the accompanying drawings, given solely by way of example:

FIG. 1 is a simplified diagram of a photometric analysis apparatus according to the invention, the apparatus being shown partly in cross-section;

FIG. 2 is a cross-section along line II—II of FIG. 1; and

DETAILED DESCRIPTION

Figure 3A:
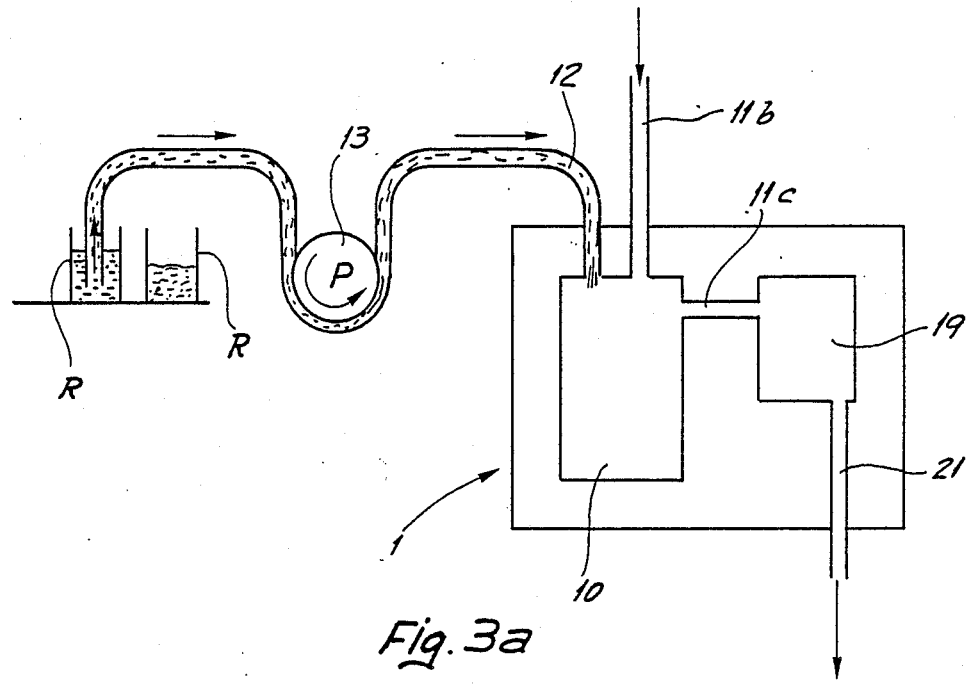
FIG. 3a and 3b illustrate operation of the analysis apparatus shown in FIGS. 1 and 2.

The apparatus shown in the drawings is here designed photometrically to analyse liquid samples following the initiation therein of a bioluminescence reaction of the type mentioned above. Such an analysis necessitates measuring the luminescence generated by the sample when it is mixed with an enzyme. This measurement may consequently be made by a photomultiplier which detects this luminescence. However, the invention is not limited to this particular application and may be applied to other optical measurements performed on successive samples, such as for example spectroscopic measurements or measurements by transparency, reflection or dispersion. If this is the case, the apparatus must include a light source able to cooperate with the photomultiplier through the liquid medium to be analysed.

The analysis apparatus shown in FIGS. 1 and 2 comprises a measuring capsule 1 fixed to the front wall of a housing 2 containing a photomultiplier 3 and a processing circuit CE connected to this photomultiplier and able to provide a signal representing the quantity of light detected during each processing cycle of a sample. The housing 2 containing the processing circuit CE may be that sold under the reference XP-2000 by Skan AG, of 4009 Basel-Alschwil, Switzerland.

The measuring capsule 1 comprises a rigid metal plate 4 screwed to the housing 2 min a manner ensuring light-tightness. The plate 4 has two cavities 5 and 6 in which are lodged respectively a measuring cell 7 and a cell 8 for the removal of the analysed sample.

The measuring cell 7 is formed of a hollow block 9 of transparent material defining a chamber 10. Three ducts 11a, 11b and 11c lead into the chamber 10. The duct 11a is provided directly in the hollow block 9 and communicates via a tube 12 with a pump 13, for example a peristaltic pump. The pump 13 is connected by a tube 14 to a pivoting arm 15 which supports a pipette 16. The arm 15 pivots on a fixed support (not shown) mounted on the frame (not shown) of the analysis apparatus. Hence, the pipette 16 can successively dip into a series of sample containers R into which samples have been put after appropriate processing. The containers R are placed on a support 17 that can be driven step-by-step (conveyor belt, rotary support or the like). Hence the pipette 16 can successively aspirate the samples out of the containers R as they travel past it. The arm is also arranged to pour liquid with an evacuation means (not shown) provided beside the support 17 after pivoting in a horizontal plane.

The duct 11b communicates with a tube end 11d which extends down into the chamber 10 with its open end near the end of the duct 11a. Adjacent the end of duct 11a the wall of chamber 10 has a turbulence recess 18.

The duct 11c constitutes an overflow for the cell 7 and is provided in the body of the rigid plate 4. It leads into a non-return chamber 19 provided in a hollow body 20 lodged in the cavity 6 of the plate. The non-return chamber 19 is connected to the evacuation system via a duct 21 in the plate.

The peristaltic pump 13 is reversible in order to allow evacuation of the measuring chamber 10.

In the illustrated embodiment of the invention, the duct 11b serves the purpose of adding an enzyme to the sample to produce therein a bioluminescence reaction. To control this addition, the duct 11b is connected to a valve 22 controlled by a control unit 23 of the analysis apparatus. The valve 22 is in turn connected to a reservoir of an enzymatic substance (not shown).

The bioluminescence reaction requires only a very small quantity of liquid sample, much less than the quantity contained in the containers R. It is hence possible to use the sample itself to remove, from the flow circuit and the measuring cell, residues of the previously analysed sample. The flushing time needed for adequate rinsing of this circuit may easily be determined as it corresponds to a given time of operation of the peristaltic pump 13. It hence suffices to start introducing the enzyme into the measuring cell at a predetermined instant at the end of this operating time to be certain that the measurement does indeed take place on a sample that is not polluted by the previous sample. In other words, the valve 22 must be open at this instant while the pump continues to operate for a given period of time. This causes, by virtue of the turbulence recess 18 situated in the neighborhood of the tube end 11d, an intimate mixture of the sample and the enzyme. The excess liquid is evacuated through the non-return chamber 19.

The reaction of the enzyme with the sample produces in the liquid contained in the measuring chamber 10 the very abrupt appearance of a certain quantity of light that is dependent the quantity of ATP released in the sample. This quantity of light is measured by the photomultiplier tube 3 which generates a measurement signal processed in the circuit CE. The latter transmits the thus-obtained data to the control unit 23.

The analysis apparatus operates as follows.

The containers R are filled with liquid samples for example biological material prepared for the bioluminescence reaction. They are placed on the conveyor 17 which is driven step-by-step in such a manner that the containers are successively placed under the arm 15. After each measurement the arm 15 drive the liquid from a previous analysis to an evacuation means situated beside the conveyor 17, by means of the pump 13.

The pipette 16 is introduced into a new container R (FIG. 3a) and the pump 13 is operated to fill the chamber 10 of the measurement cell 7 until it is completely filled and even until it overflows. The overflow liquid passes via the duct 11c into non-return chamber 19. The circulation of liquid is continued until·traces of the previous sample are eliminated; this can easily be achieved by operating the pump 13 for a sufficient time determined by the control unit 23. When this time has elapsed, the control unit opens the valve 22 to introduce into the cell 7 a given quantity of enzyme-containing solution. This solution is intimately mixed with the liquid sample which is devoid of any trace of the preceding sample. When bioluminescence is used, addition of the enzyme produces the abrupt generation of a flash of light which is transformed into an electric signal by the photomultiplier 3 for the production of visualisable data. In other types of photometric measurement, the measuring process may for example be electronically triggered after residues from the previous sample have been removed from the measurement cell.

Figure 3B:
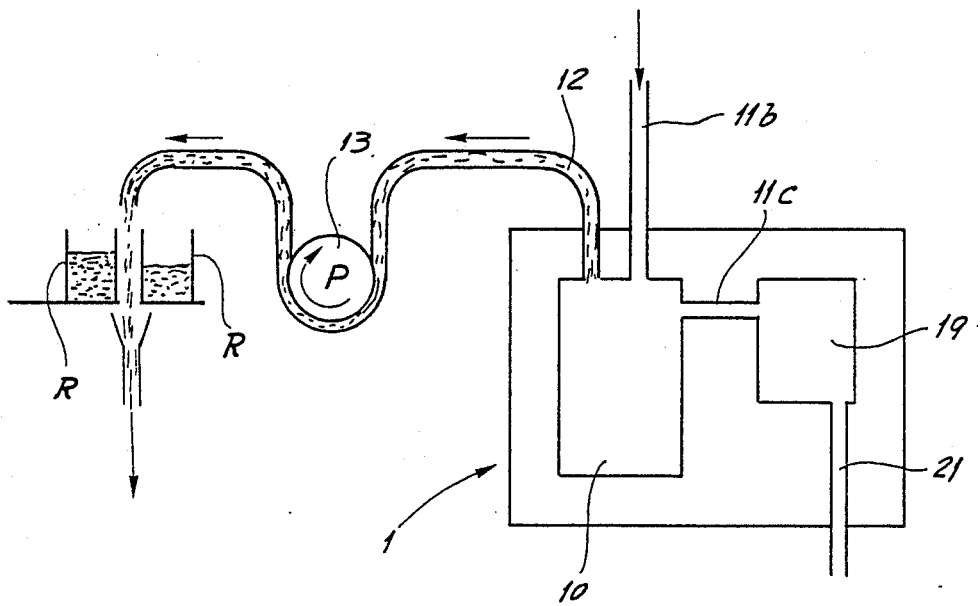

After the measurement, the cell 7 is emptied by reversing the direction of operation of the pump 13 (FIG. 3b), the non-return chamber 19 preventing any return of the liquid back into the measurement cell from the evacuation duct 21.

It is seen that, under the control unit 23, the entire operation can be automated and any risk of contamination of one sample by another is avoided by rinsing the circuit along which liquid flows by the sample which is going to be measured.

We claim:

1. Apparatus for photometrically analysing successive liquid samples, which comprises measurement cell means disposed in a light-proof enclosure and adapted to successively receive liquid samples to be analyzed, photometric detector means in said enclosure to receive a luminescent light signal representing a property of each sample and to supply an electrical signal corresponding to said light signal, and measurement processing means connected to said detector means to convert the electrical signal supplied by the detector means into data providing a visual display of said property, wherein said measurement cell means is disposed in a liquid flow circuit for successive liquid samples, said flow circuit comprising: input means for successively receiving said samples; pump means, coupled between said input means and said measurement cell means, for pumping said samples through said flow circuit; and control means, connected to said pump means, for controlling said pump means, each time a sample is to be pumped, during at least such a time interval that each sample has a volume large enough both to flush from said cell means any residue from a previous analysed sample and also to fill said cell means.

2. An apparatus according to claim 1, which further comprises triggering means for triggering the light signal in said measurement cell means after it has been completely filled with a sample or when there is an overflow of a sample into overflow means.

3. An apparatus according to claim 2, wherein said triggering means comprises duct means extending into the measurement cell means and connected to valve means for controlling the addition to the cell means of a reaction substance able to trigger a reaction producing the light signal.

4. An apparatus according to claim 3, wherein said reaction is a bioluminescence reaction and said substance is an enzymatic solution.

5. An apparatus according to claim 4, wherein said duct means for the reaction substance terminates adjacent a recess in a wall of the cell means, and the flow circuit comprises duct opening means, located in the cell and also adjacent said recess, for delivering the liquid samples to be analysed into said cell means.

6. An apparatus according to claim 1, wherein said measurement cell means is in a capsule in the form of a plate in which are provided first cavity means to lodge the measurement cell means and second cavity means in liquid communication with the measurement cell means and with liquid-evacuation means for preventing any liquid flow back into the measurement cells means when the contents thereof are emptied by said pump means.

7. An apparatus according to claim 6, wherein said capsule is mounted on a casing containing said photometric detector means and said processing means.

8. An apparatus for photometrically analyzing a succession of distinct liquid samples, said apparatus comprising:
 a light-proof enclosure;
 means, located in said light-proof enclosure, for defining therein a first cavity having a volume at most equal to the volume of each of a succession of distinct liquid samples to be analyzed;
 photometric detector means mounted in said enclosure so as to be in light-communication with said cavity, said photometric detector means being able to generate a signal representative of luminescent light generated in the liquid samples;
 input duct means connected to said cavity;
 pumping means connected to said input duct means for successively supplying thereto and to said cavity said liquid samples to be analyzed;
 control means, connected to said pump means, for controlling said pump means, each time a sample is to be pumped, during at least such a time interval that each sample has a volume large enough both to flush from the cavity any residue from a preceding sample and also to fill the cavity;
 output duct means also connected to said cavity for respectively evacuating therefrom each sample just analyzed;
 measurement processing means, connected to said photometric detector means, for converting said signal into data; and
 display means, connected to said measurement processing means so as to be responsive to data for displaying a visual representation of said data.

9. An apparatus according to claim 8 further comprising means for triggering generation of said luminescent light in each liquid sample filling said cavity.

10. An apparatus according to claim 9 wherein said triggering means comprises auxiliary duct means communicating with said cavity, and metering means, connected to said auxiliary duct means, for introducing in said auxiliary duct means a metered quantity of a reaction substance able to trigger a reaction in each liquid sample in said cavity, said reaction generating said luminescent light.

11. An apparatus according to claim 10 wherein said means for defining said first cavity comprises a recess in fluid communication with said first cavity, said input duct means and said auxiliary duct means both opening into said recess.

12. An apparatus according to claim 8 further comprising means, located in said light-proof enclosure, for defining therein a second cavity, series-connected in said output duct means, to prevent any liquid flowback into said first cavity when the contents thereof are emptied by said pump means.

13. An apparatus according to claim 12, wherein said light-proof enclosure comprises plate, having recesses therein, and a casing against which said plate is mounted, said recesses being closed by said casing.

* * * * *